§

US009848986B2

(12) United States Patent
Jones et al.

(10) Patent No.: US 9,848,986 B2
(45) Date of Patent: Dec. 26, 2017

(54) JOINT REPLACEMENT COMPONENT WITH INTEGRATED FIXATION PADS

(71) Applicant: Smith & Nephew, Inc., Memphis, TN (US)

(72) Inventors: Bob Jones, Hernando, MS (US); Vivek Pawar, Germantown, TN (US); Dean Hughes, Cordova, TN (US); Jason Jordan, Hernando, MS (US)

(73) Assignee: Smith & Nephew, Inc., Memphis, TN (US)

( * ) Notice: Subject to any disclaimer, the term of this patent is extended or adjusted under 35 U.S.C. 154(b) by 21 days.

(21) Appl. No.: 14/958,110

(22) Filed: Dec. 3, 2015

(65) Prior Publication Data

US 2016/0158016 A1   Jun. 9, 2016

Related U.S. Application Data

(60) Provisional application No. 62/087,177, filed on Dec. 3, 2014.

(51) Int. Cl.
*A61F 2/38* (2006.01)
*A61F 2/30* (2006.01)
*A61F 2/34* (2006.01)

(52) U.S. Cl.
CPC .......... *A61F 2/30767* (2013.01); *A61F 2/34* (2013.01); *A61F 2/3859* (2013.01); *A61F 2/3094* (2013.01); *A61F 2002/30014* (2013.01); *A61F 2002/3092* (2013.01); *A61F 2002/3093* (2013.01); *A61F 2002/30378* (2013.01); *A61F 2002/30451* (2013.01); *A61F 2002/30878* (2013.01); *A61F 2002/30934* (2013.01); *A61F 2210/00* (2013.01); *A61F 2310/00023* (2013.01); *A61F 2310/00029* (2013.01)

(58) Field of Classification Search
CPC ..................................................... A61F 2/3859
See application file for complete search history.

(56) References Cited

U.S. PATENT DOCUMENTS

| 5,879,398 | A  | * | 3/1999  | Swarts  | A61F 2/30907 |
|           |    |   |         |         | 623/22.21    |
| 2005/0080489 | A1 | * | 4/2005  | Estes   | A61F 2/4455  |
|           |    |   |         |         | 623/17.16    |
| 2007/0287027 | A1 | * | 12/2007 | Justin  | A61F 2/30767 |
|           |    |   |         |         | 428/666      |
| 2008/0215157 | A1 | * | 9/2008  | Earl    | A61F 2/3859  |
|           |    |   |         |         | 623/20.35    |
| 2009/0112315 | A1 | * | 4/2009  | Fang    | A61F 2/30767 |
|           |    |   |         |         | 623/11.11    |
| 2014/0277529 | A1 | * | 9/2014  | Stalcup | A61F 2/38    |
|           |    |   |         |         | 623/20.16    |

* cited by examiner

*Primary Examiner* — Thomas J Sweet
*Assistant Examiner* — Megan Wolf
(74) *Attorney, Agent, or Firm* — Taft Stettinius & Hollister LLP

(57) ABSTRACT

In one embodiment, a prosthetic component includes a plurality of fixation pads coupled to a body portion. The fixation pads may be formed of a first material suitable for attachment to bone, and the body portion may be formed of a second material different from the first material and suitable to provide a bearing surface for a joint.

18 Claims, 5 Drawing Sheets

US 9,848,986 B2

JOINT REPLACEMENT COMPONENT WITH INTEGRATED FIXATION PADS

CROSS REFERENCE TO RELATED APPLICATIONS

The present application claims the benefit of U.S. Provisional Application Ser. No. 62/087,177 filed Dec. 3, 2014, the contents of which are incorporated herein by reference in their entirety.

FIELD OF THE INVENTION

The present disclosure relates generally to prosthetic implants, and more particularly but not exclusively relates to prosthetic implants for use with human joints including knee, hip, shoulder, ankle and elbow joints.

BACKGROUND

Traditional knee or hip replacement components are typically made of cobalt chromium. The wear performance of these components is critical to proper functioning and survivorship within the body, as well as fixation with the host bone. Certain polymeric materials have the potential to decrease wear debris, but present challenges with regard to fixation with the host bone due to their flexibility and lack of bone ingrowth surfaces. Thus, there remains a need for further contributions in this area of technology.

SUMMARY

In one embodiment, a prosthetic component includes a plurality of fixation pads coupled to a body portion. The fixation pads may be formed of a first material suitable for attachment to bone, and the body portion may be formed of a second material different from the first material and suitable to create a bearing surface for a joint. Further embodiments, forms, features, and aspects of the present invention will become apparent from the detailed description and figures provided herewith.

DETAILED DESCRIPTION OF ILLUSTRATIVE EMBODIMENTS

Figure 1:
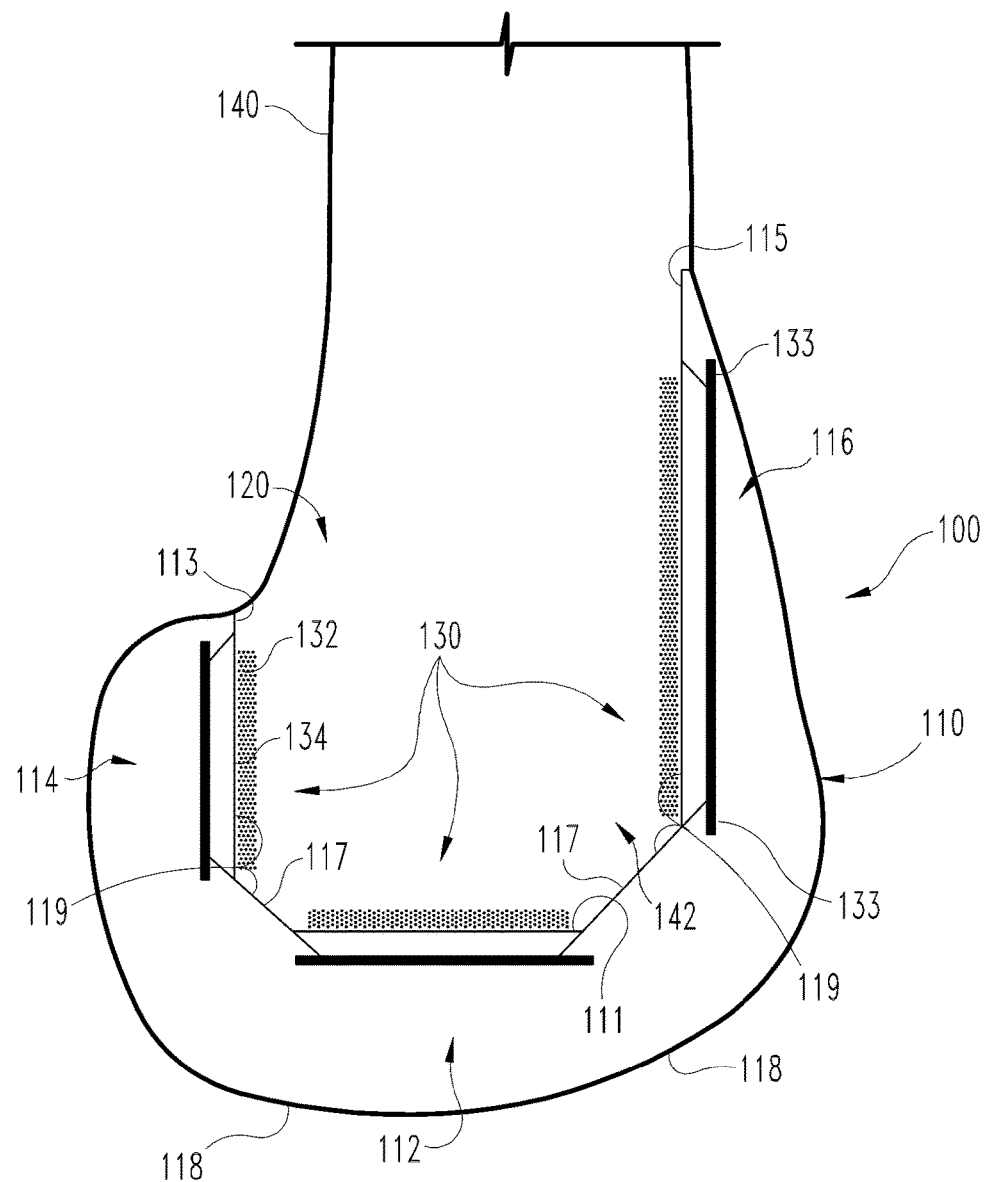
FIG. 1 is a cross-sectional schematic illustration of a femoral component according to one embodiment which includes a plurality of fixation pads.

For the purpose of promoting an understanding of the principles of the present invention, reference will now be made to the embodiments illustrated in the drawings and specific language will be used to describe the same. It will nevertheless be understood that no limitation of the scope of the invention is hereby intended. Any alterations and further modifications in the described embodiments, and any further applications of the principles of the invention as described herein are contemplated as would normally occur to one skilled in the art to which the invention relates.

The following descriptions and illustrations of non-limiting embodiments of the present invention are exemplary in nature, it being understood that the descriptions and illustrations related thereto are in no way intended to limit the inventions disclosed herein and/or their applications and uses.

With reference to FIG. 1, illustrated therein is a femoral component 100 according to one embodiment. The femoral component 100 includes a body 110 which defines an inner recess 120, and a plurality of fixation pads 130 mounted on an inner surface of the body 110 adjacent the recess 120. The body 110 is configured to replace a bearing surface of a femur 140, the recess 120 is configured to receive a resected portion 142 of the femur 140, and the fixation pads 130 are configured to couple of connect the femoral component 100 to the femur 140. As described in further detail below, the body 110 may be formed of a first material, and the fixation pads 130 may be formed of a second material different from the first material.

The body 110 generally includes a base portion 112, a posterior transverse portion 114 extending transversely from a posterior end of the base portion 112, and an anterior transverse portion 116 extending transversely from an anterior end of the base portion 112 and arranged generally opposite the posterior transverse portion 114. The anterior transverse portion 116 may be provided with a pair of condyles. An outer surface of the body 110 defines an articulating bearing surface 118, and inner surfaces 119 of the body 110 define the inner recess 120. More specifically, the inner recess 120 is defined, at least in part, by an inner surface 111 of the base portion 112, an inner surface 113 of the posterior transverse portion 114, and an inner surface 115 of the anterior transverse portion 116. The recess 120 may be further defined by chamfers 117 connecting the base portion inner surface 111 with the inner surfaces 113, 115 of the transverse portions 114, 116.

Each of the fixation pads 130 is mounted on or affixed to the inner surfaces 119 of the body 110, and includes a bone contact surface 132 which, when the femoral component 100 is implanted on the femur 140, contacts the resected portion 142 of the femur 140. The fixation pads 130 may be formed of any biocompatible material such as, for example, titanium, zirconium, cobalt chromium, and/or other suitable biocompatible materials. In the illustrated embodiment, the femoral component 100 includes a plurality of discrete fixation pads 130 such that the femoral component 100 retains some degree of the flexibility provided by the material of the body 110 which may, for example, constitute a polymeric material. As a result, the flexibility of the femoral component 100 may be greater than that available with a traditional femoral component formed of a metallic material. In other embodiments, as discussed below, a single fixation pad may be formed along substantially the entirety of the inner surface 119 so as to increase the rigidity of the femoral component 100.

In the illustrated embodiment, the bone contacting surfaces 132 are configured as porous bone ingrowth surfaces 134 structured to allow bone or bone tissue of the femur 140 to grow on and/or into the fixation pads 130 and become integrated with the fixation pads 130. In other embodiments, the bone contacting surfaces 132 may be configured to be affixed to the femur 140 by cement or another type of fixation material. In embodiments in which the fixation pads 130 include the bone ingrowth surfaces 134, the bone ingrowth surfaces 134 may be formed of any biocompatible material such as, for example, titanium, zirconium, cobalt chromium, and/or other suitable biocompatible materials. Additionally, the bone ingrowth surfaces 134 may be treated with a material that promotes bone ingrowth such as, for example, a bone morphogenetic protein (BMP), hydroxyapatite or other types of materials that promote bone ingrowth.

Various properties of the femoral component 100 may be tailored/designed to a particular set of operating parameters such as, for example, desired flexibility and fixation strength, by selecting appropriate materials and geometries for the body 110 and the fixation pads 130. For example, the material and thickness of the body 110 may be selected to provide a desired amount of flexibility and/or wear resistance. In certain embodiments, the body 110 may be formed of a polymeric or plastic material such as, for example, polyether ether ketone (PEEK). The polymeric material of the body 110 may be surface treated to increase the wettability of the surface and/or to improve resistance to wear. Additionally, ceramic particulates such as, for example, alumina or zirconia may be embedded in the polymeric substrate to optimize the stiffness of the body 110 along with bone in-growth or on-growth materials such as hydroxyapatite. In certain embodiments, the body 110 may be formed of two or more polymeric materials or other combinations of materials. In other embodiments, antimicrobial agents such as, for example, silver, copper or zinc can be incorporated into the body 110 to promote infection resistance. Such agents may be incorporated using standard manufacturing processes such as, for example, physical or chemical vapor deposition or wet chemistry (i.e., depositing from silver, copper or zinc salts).

In the illustrated form, the body 110 is formed primarily of a polymeric or plastic material, and the fixation pads 130 are formed of a biocompatible metallic material. In other embodiments, the body 110 may be formed of a biocompatible metallic material, and/or the one or more of the fixation pads 130 may be formed of a polymeric or plastic material. For example, the body 110 may be formed of cobalt chromium, and each of the fixation pads 130 may be formed of PEEK.

Figure 2:
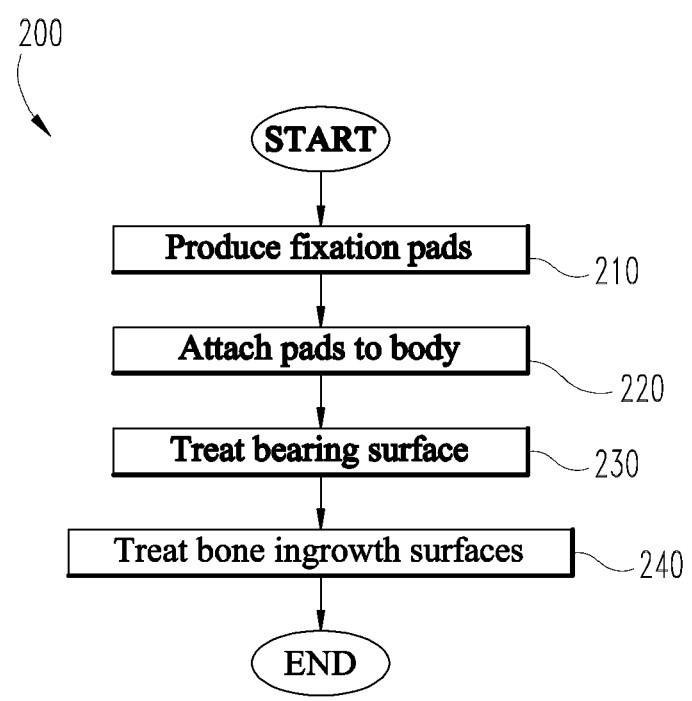
FIG. 2 is a schematic flow diagram of a process for creating a femoral component according to one embodiment.

With additional reference to FIG. 2, illustrated therein is an illustrative process 200 for creating a joint replacement component such as, for example, the femoral component 100. Operations/steps illustrated for the processes in the present application are understood to be exemplary only, and the operations/steps may be combined, divided, added or removed, as well as re-ordered in whole or in part, unless explicitly stated to the contrary.

The process 200 begins with an operation 210, which includes forming the fixation pads 130. The operation 210 may include forming or producing the fixation pads 130 by any suitable manufacturing process such as, for example, laser printing, machining, sintering beads, metal injection molding, casting, and/or other suitable processes. The operation 210 may further include forming a porous bone ingrowth surface such as, for example, in embodiments in which the fixation pads 130 include the bone ingrowth surfaces 134.

Once the fixation pads 130 are produced, the process 200 continues to an operation 220 which includes attaching the fixation pads 130 to the body 110 of the femoral component 100. In certain embodiments, the operation 220 may include molding the polymeric material around the fixation pads 130 to form the body 110. In other embodiments, the body 110 may be pre-formed, and the operation 220 may include pressing the fixation pads 130 into the body 110 at selected locations such as, for example, using heat and pressure. In another embodiment, a solid structure may be built on the porous fixation pads 130 using laser or electron beam sintering methods. The fixation pads 130 may also include features which increase the strength of the attachment/fixation between the fixation pads 130 and the polymeric material of the body 110. For example, in embodiments in which the operation 220 includes molding the polymeric material around the fixation pads 130, the fixation pads 130 may include flanges or dovetail connections 133 about which the polymeric material is molded, thereby securely retaining the position of the fixation pads 130 on the body 110.

The process 200 further includes an operation 230 which includes treating the bearing surface 118. The operation 230 may include, for example, treating the bearing surface 118 with a coating configured to increase wettability and/or decrease wear. In embodiments in which the fixation pads 130 include the bone ingrowth surfaces 134, the process 200 may further include an operation 240 of treating the bone ingrowth surfaces 134 with a coating configured to promote bone ingrowth such as, for example, treating the bone ingrowth surfaces 134 with BMP, hydroxyapatite or another suitable bone growth promoting material.

FIGS. 3-6 depict femoral components 300, 400, 500 and 600 according to other embodiments. Each of the femoral components is configured substantially similar to the femoral component 100 illustrated in FIG. 1 and described above. Unless indicated otherwise, similar reference characters are used to indicate similar elements and features. In the interest of conciseness, the following descriptions focus primarily on features that are different than those described above with regard to the femoral component 100.

Figure 3:
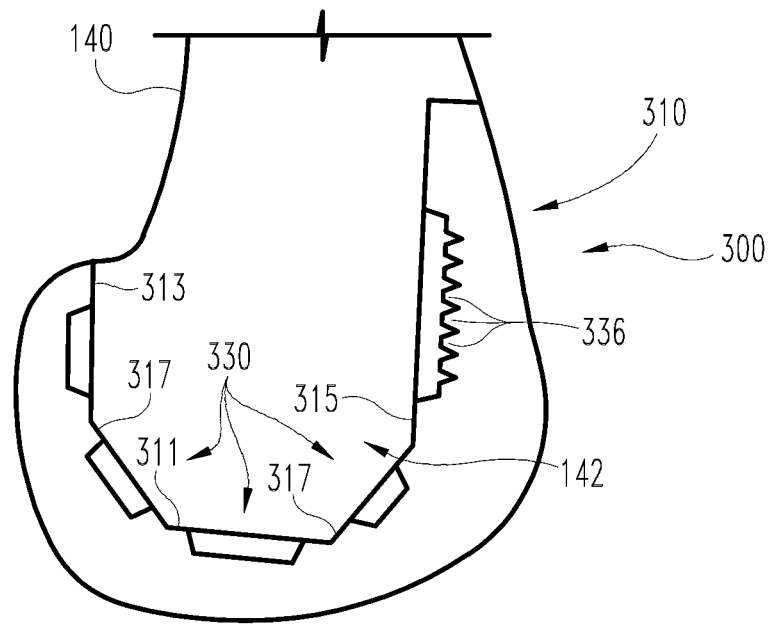
FIG. 3 is a cross-sectional illustration of a femoral component according to another embodiment which includes a plurality of fixation pads.

With particular reference to FIG. 3, illustrated therein is a femoral component 300 according to another embodiment which includes a plurality of discrete fixation pads 330 coupled with the body 310, each of which is mounted to one of the surfaces 311, 313, 315, 317 of the inner surfaces of the body 310. The fixation pads 330 may include a porous surface configured to promote bone ingrowth, and/or may be affixed to the resected portion 142 of the femur 140 by a cement material 336.

Figure 4:
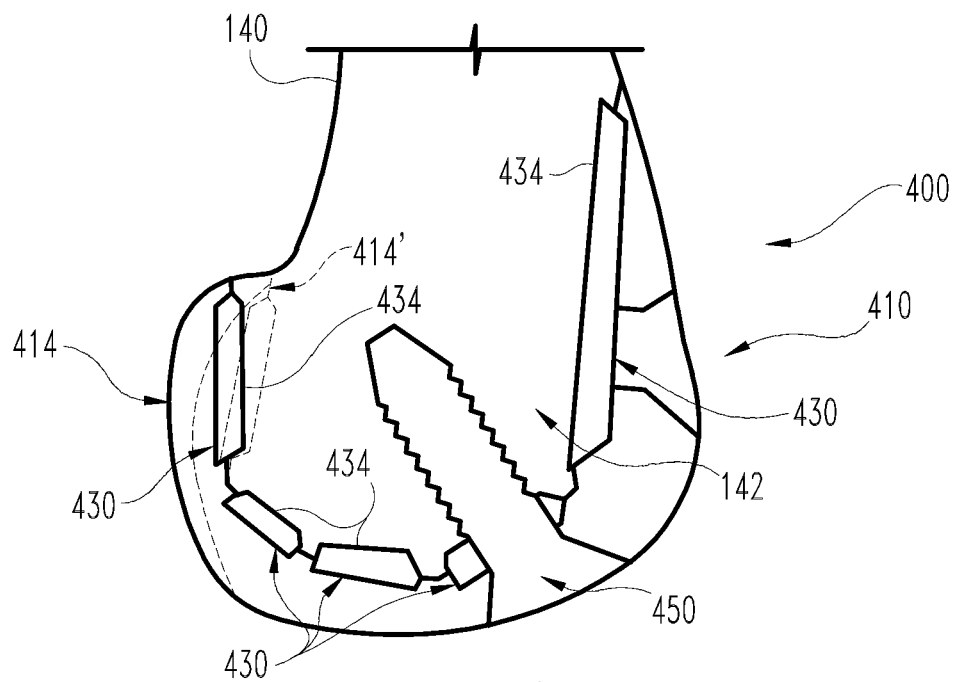
FIG. 4 is a cross-sectional illustration of a femoral component according to yet another embodiment which includes fixation features that retain the femoral component in position on a femur.

With particular reference to FIG. 4, illustrated therein is a femoral component 400 according to another embodiment which includes a plurality of fixation pads 430 coupled with the body 410 and including bone ingrowth surfaces 434. The femoral component 400 also includes features which retain the position of the femoral component 400 on the femur 140 until bone ingrowth fixedly couples the fixation pads 430 with the femur 140. For example, the posterior transverse portion 414 may be angled toward the anterior transverse portion 416, as depicted in phantom via element 414'.

During implantation of the femoral component 400 onto the femur 140, the resected portion 142 of the femur 140 may be inserted into the opening 420 at an angle, and the femoral component 400 may then be rotated/rolled and pressed onto the resected portion 142 of the femur 140 such that the posterior transverse portion 414, 414' flexes in an outward direction. With the resected portion 142 received in the opening 420, the elastically deformed posterior transverse portion 414, 414' inhibits movement of the femoral component 400 with respect to the femur 140. The femoral component 400 may additionally or alternatively be further affixed or attached to the femur 140 by a peg or a screw 450 which may optionally pass through one of the fixation pads 430.

Figure 5:
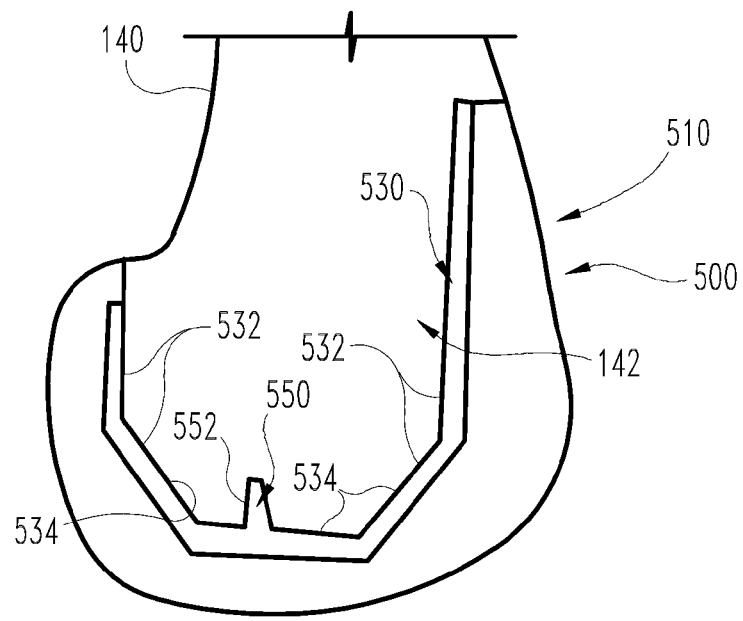
FIG. 5 is a cross-sectional illustration of a femoral component according to yet another embodiment which includes a single, continuous fixation pad and fixation features that retain the femoral component in position on a femur.

With particular reference to FIG. 5, illustrated therein is a femoral component 500 according to another embodiment which includes a single fixation pad 530 that is coupled with the body 510 and positioned in contact with substantially the entire surface of the resected portion 142 of the femur 140. The fixation pad 530 includes a plurality of contact surfaces 532 which may but need not necessarily include a porous bone ingrowth surface 534. Additionally, the femoral component 500 includes a fixation peg 550 which aids in retaining the femoral component 500 in position on the femur 140. The fixation peg 550 may be integrally formed with the fixation pad 530 to define a unitary single-piece element, and/or the fixation peg 550 may include a porous bone ingrowth surface 552.

Figure 6:
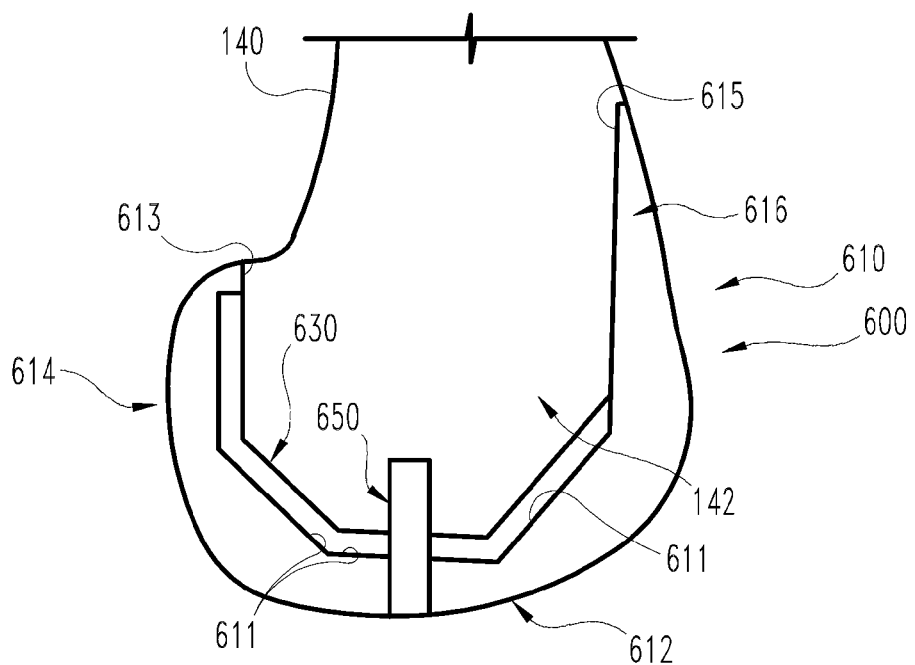
FIG. 6 is a cross-sectional illustration of a femoral component according to yet another embodiment which includes a single, continuous fixation pad and fixation features that retain the femoral component in position on a femur.

With particular reference to FIG. 6, illustrated therein is a femoral component 600 according to another embodiment which includes a single fixation pad 630 coupled with the body 610 that is in contact with only a portion of the surface of the resected portion 142 of the femur 140. In the illustrated embodiment, the fixation pad 630 extends along the inner surface 613 of the posterior transverse portion 614, and along the inner surfaces 611 of the base portion 612, but does not extend along the inner surface 615 of the anterior transverse portion 616. In another embodiment, it is also contemplated that the fixation pad 630 may extend along the inner surface 615 of the anterior transverse portion 616 and along the inner surfaces 611 of the base portion 612, but need not necessarily extend along the inner surface 613 of the posterior transverse portion 614. The femoral component 600 also includes a fixation peg 650 which aids in retaining the femoral component 600 in position on the femur 140. The fixation peg 650 may, for example, extend through the base portion 612 and a corresponding portion of the fixation pad 630.

Figure 7:
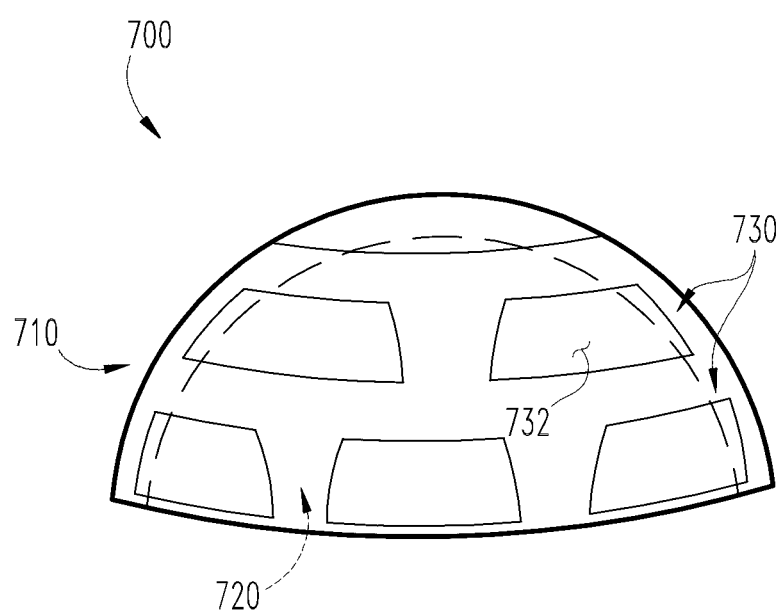
FIG. 7 is an illustration of an acetabular component according to one embodiment which includes a plurality of fixation pads.

While the above-described femoral components 100-600 are configured as femoral components configured for use in association with a knee joint, components according to other embodiments may be configured for use with other joints such as, for example, a hip, shoulder, ankle, or elbow joint. For example, FIG. 7 depicts an acetabular component 700 configured for use in association with a hip joint. The acetabular component 700 includes a dome-shaped or hemispherical body 710 defining an interior socket 720 configured to receive a femoral head, and a plurality of fixation pads 730 affixed to an exterior surface of the body 710 for contact with bone tissue when the component is attached to bone.

The body 710 and the fixation pads 730 may be formed of similar materials and in a similar manner as described above with reference to FIGS. 1 and 2. For example, the body 710 may be formed of a polymeric material, and the fixation pads 730 may be configured for a cemented connection to a pelvis, and/or may be adapted to promote bone ingrowth into the bone contact surfaces 732. Additionally, while the illustrated acetabular component 700 includes a plurality of discrete fixation pads 730, it is also contemplated that the component may include a single fixation pad extending at least partially about the body 710. For example, the component 700 may include a single dome-shaped fixation pad sized to cover substantially the entire exterior surface of the body 710.

Various changes and modifications to the described embodiments described herein will be apparent to those skilled in the art, and such changes and modifications can be made without departing from the spirit and scope of the invention and without diminishing its intended advantages. Additionally, while the invention has been illustrated and described in detail in the drawings and foregoing description, the same is to be considered illustrative and not restrictive in character, it being understood that only selected embodiments have been shown and described and that all changes, equivalents, and modifications that come within the scope of the inventions described herein or defined by the following claims are desired to be protected.

What is claimed is:

1. A prosthetic component, comprising:
   a body portion sized and configured to replace a portion of a bone in a joint, and including a bearing side and an opposite bone-facing side, wherein the body portion is formed of a first material, wherein the bone-facing side includes a plurality of bone-facing surfaces including a first bone-facing surface and a second bone-facing surface, and wherein the first bone-facing surface and the second bone-facing surface are angularly offset from one another; and
   a plurality of discrete fixation pads coupled to the bone-facing side, wherein each of the fixation pads includes an attachment surface configured for attachment to bone, wherein each of the fixation pads is formed of a second material having a greater rigidity than the first material;
   wherein each of the first material and the second material comprises a material selected from the group consisting of a polymeric material, a plastic material, a ceramic material, and a metallic material;
   wherein a first of the discrete fixation pads is coupled to the first bone-facing surface, and a second of the discrete fixation pads is coupled to the second bone-facing surface such that a gap is formed between the first fixation pad and the second fixation pad, the gap permitting flexing of the prosthetic component to alter the angular offset of the first bone-facing surface relative to the second bone-facing surface; and
   wherein the body portion is molded onto the fixation pads such that the fixation pads are fixedly coupled with the body portion.

2. The prosthetic component of claim 1, wherein the first material comprises the polymeric material, and the second material comprises the metallic material.

3. The prosthetic component of claim 2, wherein the first material further comprises ceramic particulates embedded in the polymeric material.

4. The prosthetic component of claim 2, wherein the polymeric material comprises polyether ether ketone (PEEK).

5. The prosthetic component of claim 1, wherein the attachment surface is configured to be attached to bone by a cement.

6. The prosthetic component of claim 1, wherein the attachment surface is a porous bone ingrowth surface.

7. The prosthetic component of claim 6, wherein the porous bone ingrowth surface is treated with a material configured to promote bone ingrowth.

8. The prosthetic component of claim 1, wherein the attachment surface is treated with an antimicrobial agent to promote infection resistance, the antimicrobial agent comprising at least one of silver, copper and zinc.

9. The prosthetic component of claim 1, wherein the second fixation pad covers substantially the entire second bone-facing surface.

10. A prosthetic component, comprising:
a body sized and configured to replace a portion of a bone in a joint, the body including an outer surface and a recess configured to receive a resected bone, wherein the recess is defined at least in part by a plurality of bone-facing surfaces, and wherein the body is formed of a polymeric material; and
a plurality of discrete fixation pads, wherein each fixation pad is coupled to a corresponding one of the bone-facing surfaces such that one or more gaps are formed between the plurality of discrete fixation pads, wherein each fixation pad is formed of a biocompatible metallic material and comprises a bone contacting surface configured for attachment to bone;
wherein the body is molded onto the fixation pads such that the fixation pads are fixedly coupled with the body.

11. The prosthetic component of claim 10, wherein the plurality of bone-facing surfaces comprises a first inner surface formed at a base portion of the body, a second inner surface formed at an anterior transverse portion of the body, and a third inner surface formed at a posterior transverse portion of the body.

12. The prosthetic component of claim 11, wherein each of the first inner surface, the second inner surface, and the third inner surface has at least one of the plurality of discrete fixation pads coupled thereto.

13. The prosthetic component of claim 12, wherein the third inner surface is angled toward the second inner surface, and wherein the discrete fixation pads permit the posterior transverse portion to flex in a direction away from the anterior transverse portion.

14. The prosthetic component of claim 11, wherein a first of the fixation pads includes an opening structured to receive at least one of a screw and a peg.

15. The prosthetic component of claim 11, wherein a first of the fixation pads is coupled to the first inner surface and includes a fixation peg extending into the recess.

16. A method, comprising:
forming a plurality of fixation pads of a metallic material;
forming a body of a polymeric material, wherein forming the body includes forming the body with a bearing surface, a first bone-facing surface, and a second bone-facing surface that is angularly offset from the first bone-facing surface, the polymeric material having a greater flexibility than the metallic material;
attaching a first of the fixation pads to the first bone-facing surface; and
attaching a second of the fixation pads to the second bone-facing surface such that a gap is formed between the first and second fixation pads;
wherein the gap permits relative flexing of the first and second bone-facing surfaces; and
wherein forming the body includes molding the polymeric material around the fixation pads, thereby attaching the first fixation pad and the second fixation pad to the first bone-facing surface and the second bone-facing surface, respectively.

17. The method of claim 16, wherein forming the plurality of fixation pads includes forming a bone ingrowth surface on each fixation pad, and wherein the method further comprises treating each bone ingrowth surface with a material configured to promote bone ingrowth.

18. The method of claim 16, wherein forming the plurality of fixation pads includes incorporating one or more antimicrobial agents for infection resistance.

* * * * *